United States Patent
Ulvestad et al.

(10) Patent No.: US 10,078,305 B2
(45) Date of Patent: Sep. 18, 2018

(54) METHOD FOR PHASE RETRIEVAL TO REDUCE A SAMPLING REQUIREMENT WHEN IMAGING A DYNAMIC PROCESS

(71) Applicant: UChicago Argonne, LLC, Chicago, IL (US)

(72) Inventors: Andrew P. Ulvestad, Lemont, IL (US); Stephan O. Hruszkewycz, Chicago, IL (US); Paul H. Fuoss, Oak Park, IL (US); Stefan M. Wild, Downers Grove, IL (US); Ashish Tripathi, Lemont, IL (US)

(73) Assignee: UChicago Argonne, LLC, Chicago, IL (US)

( * ) Notice: Subject to any disclaimer, the term of this patent is extended or adjusted under 35 U.S.C. 154(b) by 159 days.

(21) Appl. No.: 15/294,314

(22) Filed: Oct. 14, 2016

(65) Prior Publication Data
US 2018/0107160 A1    Apr. 19, 2018

(51) Int. Cl.
*H04N 13/20*    (2018.01)
*G01N 21/41*    (2006.01)
(Continued)

(52) U.S. Cl.
CPC ....... *G03H 1/0866* (2013.01); *G01N 21/4788* (2013.01); *G03H 1/0402* (2013.01); *G03H 2001/0428* (2013.01); *G03H 2001/0441* (2013.01); *G03H 2001/0875* (2013.01); *G03H 2001/0883* (2013.01)

(58) Field of Classification Search
CPC ............. G03H 1/0886; G03H 1/0402; G03H 2001/0428; G03H 2001/0441; G03H 2001/0875; G01N 121/4788
See application file for complete search history.

(56) References Cited

U.S. PATENT DOCUMENTS 9,401,042 B2 *    7/2016    Rodenburg ............ A61B 6/027
2015/0192510 A1 *    7/2015    Piestun ................. G01B 11/002
702/151
(Continued)

OTHER PUBLICATIONS

Chapman et al., High-Resolution Ab Initio Three-Dimensional X-Ray Diffraction Microscopy, May 2006, 22 pages.
(Continued)

*Primary Examiner* — Jessica M Prince
(74) *Attorney, Agent, or Firm* — Foley & Lardner LLP

(57) ABSTRACT

A method for retrieving phase information in a coherent diffraction imaging process includes acquiring a plurality of 3D data sets, each 3D data set corresponding to one of a plurality of time states, and reconstructing a 3D image of the object at a given time state using the 3D data set from all of the time states. Each 3D data set is acquired by: illuminating an object positioned in a first position with a coherent beam; measuring a first 2D diffraction pattern using an area detector; rotating the object around a tilt axis thereof to a second position that is different from the first position; re-illuminating the object positioned in the second position with the coherent beam; re-measuring a second 2D diffraction pattern using the area detector; and repeating the rotating, re-illuminating and re-measuring steps such that each 3D data set includes a predetermined number of diffraction patterns.

11 Claims, 14 Drawing Sheets

(51) Int. Cl.
  *G03H 1/08*   (2006.01)
  *G01N 21/47*  (2006.01)
  *G03H 1/04*   (2006.01)

(56) References Cited

U.S. PATENT DOCUMENTS

2016/0266057 A1* 9/2016 Dudovich ............ G03H 1/0866
2017/0184483 A1* 6/2017 Bartels ............... G01N 15/1434

OTHER PUBLICATIONS

Fienup et al., Phase-Retrieval Stagnation Problems and Solutions, Nov. 1986, 11 pages.
Marchesini, Invited Article: A Unified Evaluation of Iterative Projection Algorithms for Phase Retrieval, 2007, 10 pages.

* cited by examiner

FIG. 1(A)
BCDI rocking curve
FIG. 1(B)
Select states
t=12 min
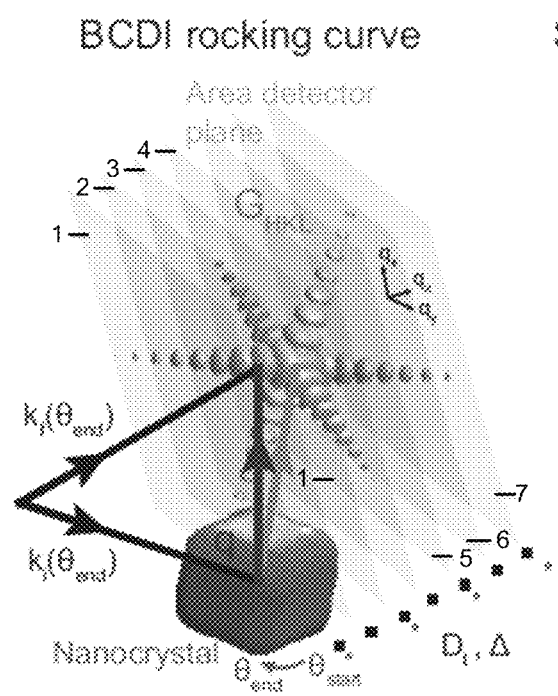
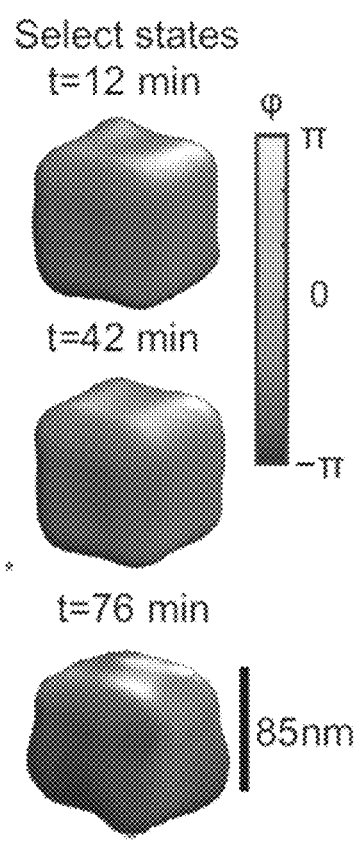
t=42 min
t=76 min
85nm

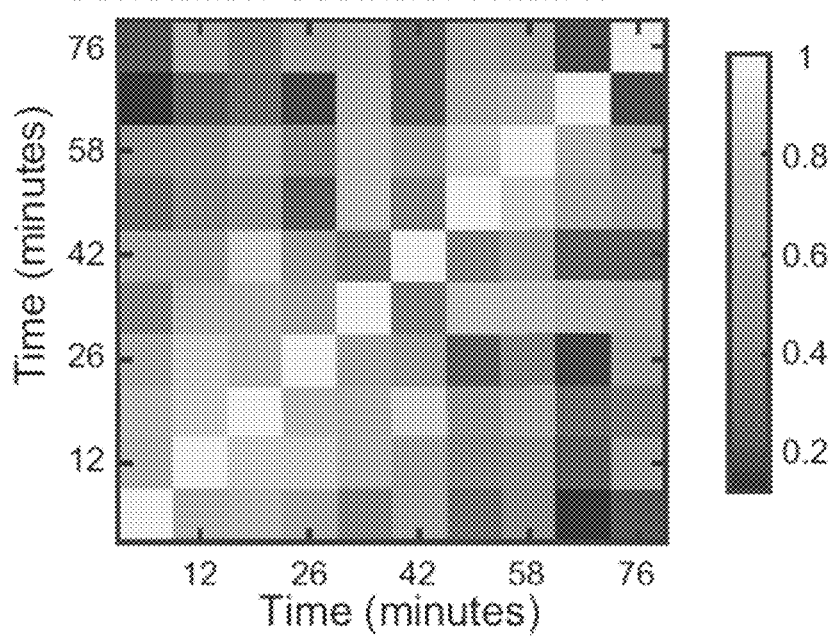

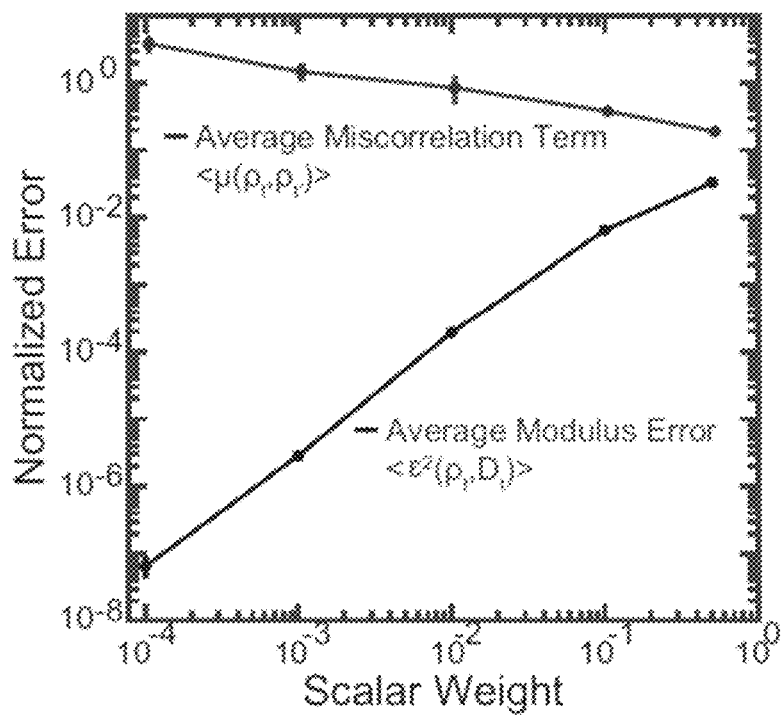

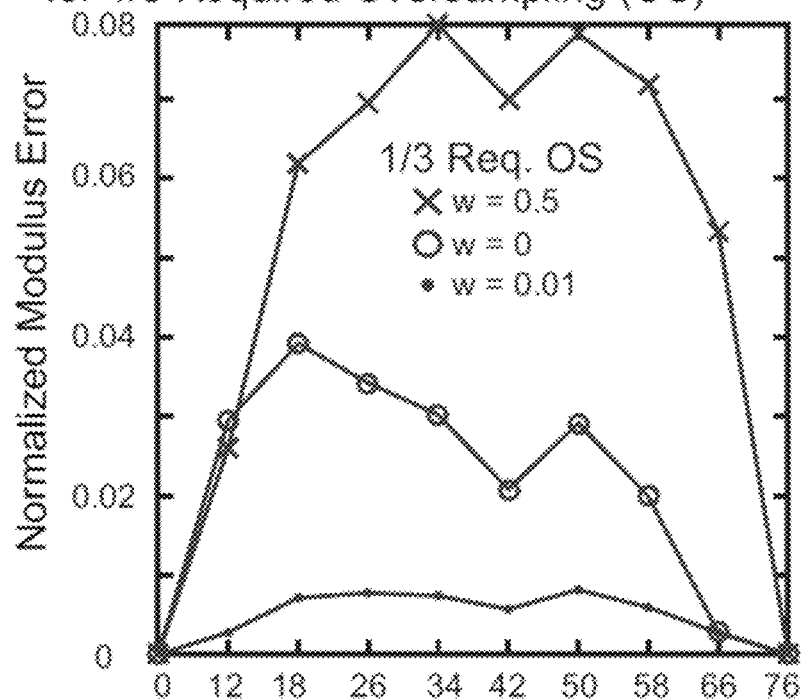

Reconstructions of Real Data with 1/2 Req. OS
FIG. 6(A): t= 12 min
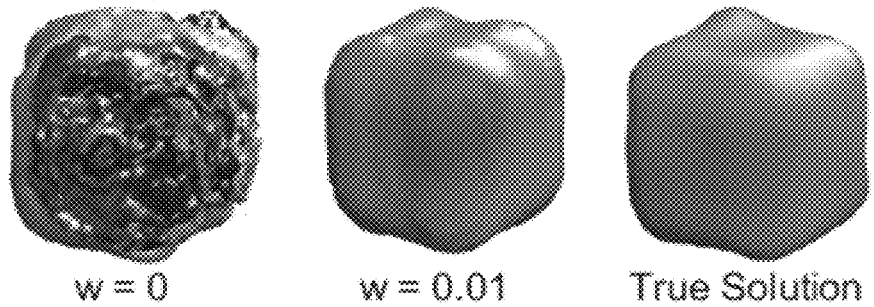
w = 0         w = 0.01        True Solution
FIG. 6(B): t= 42 min
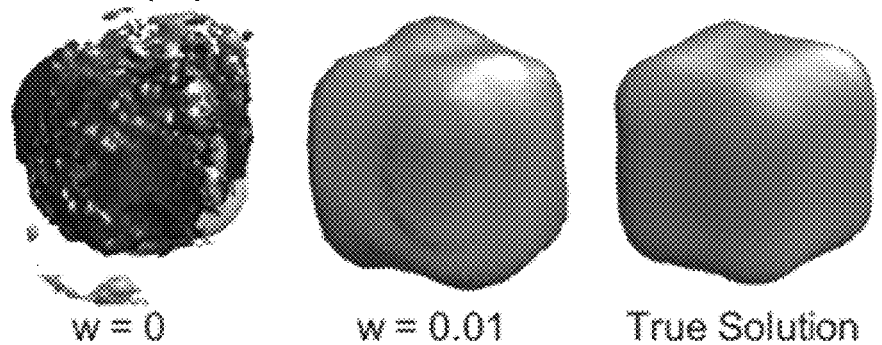
w = 0         w = 0.01        True Solution
FIG. 6(C): t= 66 min
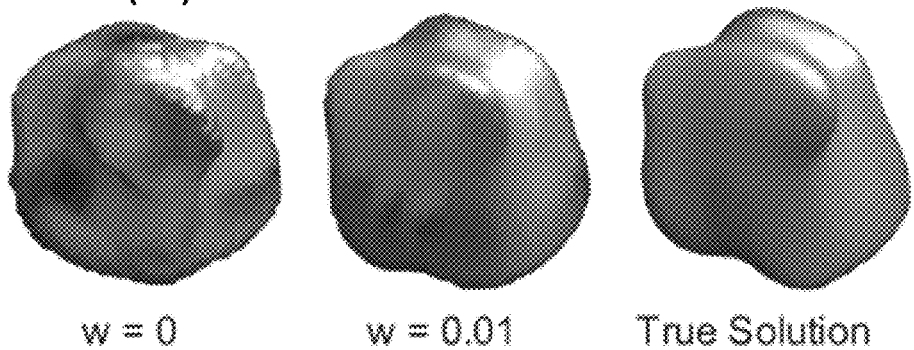
w = 0         w = 0.01        True Solution
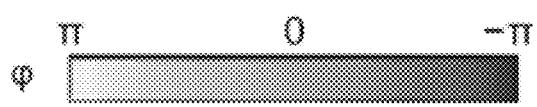

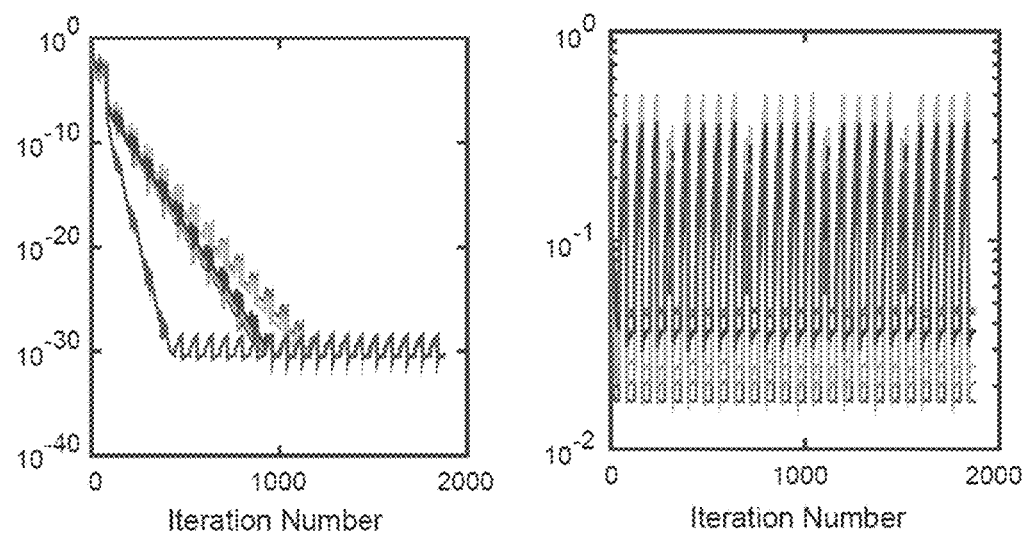
FIG. 8(A): w=0                FIG. 8(B): w=0.5

FIG. 9(A): t=12 min
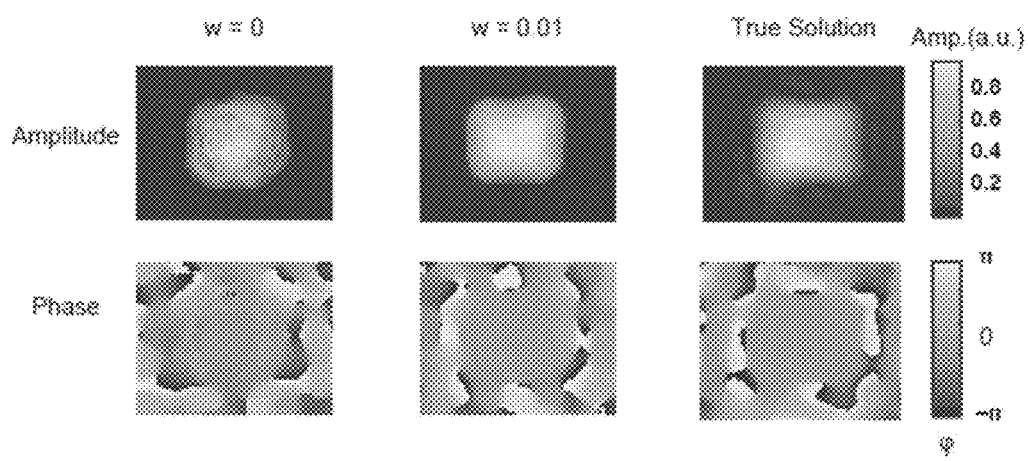
FIG. 9(B): t=42 min
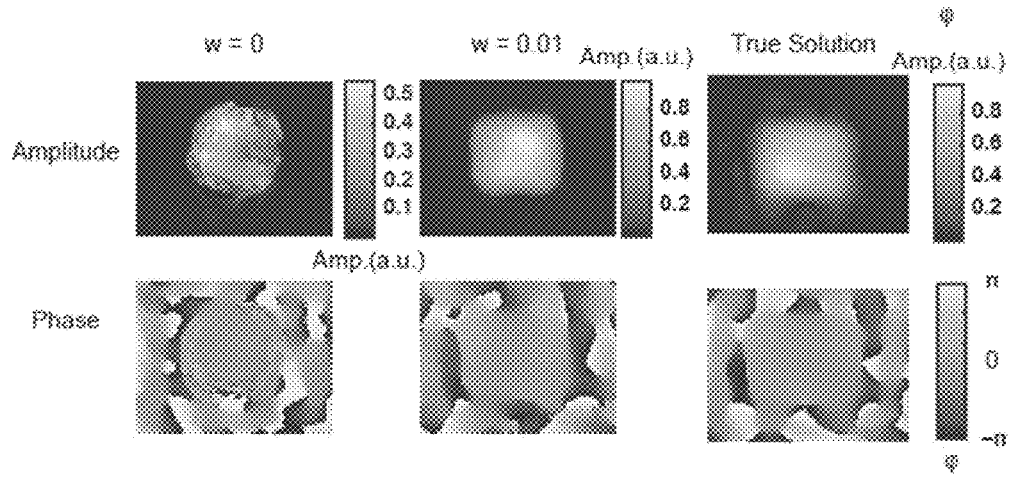

METHOD FOR PHASE RETRIEVAL TO REDUCE A SAMPLING REQUIREMENT WHEN IMAGING A DYNAMIC PROCESS

STATEMENT OF GOVERNMENT INTEREST

The United States Government claims certain rights in this invention pursuant to Contract No. DE-AC02-06CH11357 between the U.S. Department of Energy and UChicago Argonne, LLC, as operator of Argonne National Laboratories.

FIELD OF THE INVENTION

The present invention relates generally to the field of imaging techniques that do not produce an image directly. More specifically, the present invention relates to a method for phase retrieval in an imaging technique, in particular, to phase retrieval during a dynamic process.

BACKGROUND

This section is intended to provide a background or context to the invention recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Understanding nanoscale processes is key to improving the performance of advanced technologies, such as batteries, catalysts, and fuel cells. However, many processes occur inside devices at short length and time scales in reactive environments and represent a significant imaging challenge. One way to study such structures is by using coherent diffraction imaging (CDI). CDI is a lensless technique for reconstructing a 3D image of an object based on a diffraction pattern. In CDI, a coherent beam of x-rays or electrons is incident on an object, the beam scattered by the object produces a diffraction pattern that is measured by an area detector, and an image is reconstructed from the diffraction pattern. When the diffraction pattern is measured by the area detector, the data is based on a number of counts of photons or electrons. This gives rise to the "phase problem" or loss of phase information when a diffraction pattern is collected. In order to recover the phase information, Fourier-based iterative phase retrieval algorithms are utilized.

Another example of CDI is Bragg coherent diffractive imaging (BCDI). In BCDI, the object is rotated around a tilt axis and a sequence of 2D diffraction patterns are measured at different sample orientations. BCDI is a powerful technique for investigating dynamic nanoscale processes in nanoparticles immersed in reactive, realistic environments. With current BCDI methods, 3D image reconstructions of nanoscale crystals have been used to identify and track dislocations image cathode lattice strain during battery operation, indicate the presence of surface adsorbates, and reveal twin domains. The temporal resolution of current BCDI experiments, however, is limited by the oversampling requirements for current phase retrieval algorithms.

Conventional phase retrieval algorithms present a problem in improving the time resolution of an imaging technique (e.g., CDI, BCDI, etc.). The imaging technique requires a computer algorithm to convert the experimental data into a real space image of the object (e.g., nanocrystals) in reactive environments. Oversampling refers to the number of measurements that are required to faithfully reproduce the image. The autocorrelation of the image must be sampled at the Nyquist frequency, which is twice the highest frequency in the system. Because each measurement takes time, the oversampling requirement results in a lengthy process that may include prolonged radiation dose. Moreover, if the oversampling requirement is too high, it may not be possible to image a dynamic process such as crystal growth, catalysis or strain in battery cathode nanoparticles that occur too rapidly (i.e., faster than the amount of time it takes to satisfy the oversampling requirements).

A need exists for improved technology, including a method for phase retrieval that allows for the time resolution to be improved, for example, by reducing the oversampling requirement at each time step.

SUMMARY

One embodiment of the invention relates to a method for retrieving phase information in a coherent diffraction imaging process. The method includes acquiring a plurality of 3D data sets, each 3D data set corresponding to one of a plurality of time states and reconstructing a 3D image of the object at a given time state using information from the 3D data set from the given time state and all of the other time states. Each 3D data set is acquired using the following steps: illuminating an object to be imaged with a coherent beam, the object positioned in a first position; measuring a first 2D diffraction pattern using an area detector that detects a number of photons or electrons in a beam scattered by the object; rotating the object around a tilt axis thereof to a second position that is different from the first position; re-illuminating the object with the coherent beam, the object positioned in the second position; re-measuring a second 2D diffraction pattern using the area detector; and repeating the rotating, re-illuminating and re-measuring steps a predetermined number of times such that each 3D data set includes a predetermined number of diffraction patterns.

In some aspects, the predetermined number of diffraction patterns in at least one 3D data set is less than a minimum number of 2D diffraction patterns required based on the Nyquist frequency. The 3D image reconstructed based on the at least one 3D data set has image fidelity, where image fidelity is established when a sum of a difference between a real image and the 3D image reconstructed based on the at least one 3D data set on a pixel by pixel basis is less than or equal to a predetermined level of acceptable error. The predetermined level of acceptable error may be, for example, less than or equal to 10% per pixel.

In some aspects, the predetermined number of diffraction patterns in at least one 3D data set is ⅓ of a minimum number of 2D diffraction patterns required based on the Nyquist frequency.

In some aspects, the plurality of 3D data sets include a 3D data set acquired at an initial time state, a 3D data set acquired at a final time state, and at least one 3D data set acquired at an intermediate time state between the initial time state and the final time state.

In some aspects, the predetermined number of diffraction patterns in the initial time state is equal to a minimum number of 2D diffraction patterns required based on the Nyquist frequency. The predetermined number of diffraction patterns in the final time state is equal to the minimum number of 2D diffraction patterns required based on the Nyquist frequency. The predetermined number of diffraction patterns in the intermediate time state is less than to the minimum number of 2D diffraction patterns required based on the Nyquist frequency.

In some aspects, the object is a nanocrystal having a size, for example, of 100-500 nm. The step of reconstructing the 3D image of the nanocrystal is repeated for each of the plurality of time states to produce a series of 3D images that show a change in a structure of the nanocrystal over time.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The disclosure will become more fully understood from the following detailed description, taken in conjunction with the accompanying figures, in which:

FIG. 1(A) illustrates a Bragg coherent diffractive imaging (BCDI) experiment of a single time-evolving nanocrystal. In particular, FIG. 1(A) is a schematic illustration of a Bragg rocking curve that sweeps the 2D area detector through the 3D volume in the $q_z$ direction.

FIG. 1(B) illustrates a Bragg coherent diffractive imaging (BCDI) experiment of a single time-evolving nanocrystal. In particular, FIG. 1(B) illustrates select time states from a time sequence that was reconstructed from experimental BCDI data measured with greater than the required oversampling.

FIG. 3(A) illustrates a time correlation in the [111] displacement field projection $u_{111}(r)$ during the reconstructed time sequence.

FIG. 3(B) illustrates an average (over all time states and random starts) modulus error and average (over all time states and random starts) miscorrelation term normalized by the total intensity in the image as a function of the scalar weight. Error bars represent the standard deviation of the average over all time states obtained from ten different random starts.

FIG. 4(A) illustrates the average (over all time states and random starts) normalized modulus error as a function of the scalar weight w for ⅓, 1/20, and 1/84 of the required oversampling. The modulus error reported here is computed with respect to the data with the required oversampling. Error bars represent the standard deviation of the different average (over all time states) values obtained from ten different random starts. The error bar for w=0.01 and 1/20th of the required oversampling is offset for clarity. The black dashed horizontal line shows the normalized average modulus error using the average of the initial and final time states for every time state in the sequence.

FIG. 4(B) illustrates the results for reduced oversampling. In particular, FIG. 4(B) illustrates the individual time state errors for ⅓ required oversampling for a particular random start for w=0 (open circle), w=0.01 (points), and w=0.5 (x).

FIG. 6(A) illustrates reconstructions of experimental measurement data with reduced oversampling. The real part of the image (shown as an isosurface) corresponds to the reconstructed Bragg electron density, while the complex part of the image (gradient map projected onto the isosurface) corresponds to the reconstructed displacement field projection. In particular, FIG. 6(A) illustrates the t=12 min reconstructions for ½ of the required oversampling for w=0 and w=0.01, and the true solution, which is reconstructed using the complete data set.

FIG. 6(B) illustrates reconstructions of experimental measurement data with reduced oversampling. The real part of the image (shown as an isosurface) corresponds to the reconstructed Bragg electron density, while the complex part of the image (gradient map projected onto the isosurface) corresponds to the reconstructed displacement field projection. In particular, FIG. 6(B) illustrates the t=42 min reconstructions for ½ of the required oversampling for w=0 and w=0.01, and the true solution, which is reconstructed using the complete data set.

FIG. 6(C) illustrates reconstructions of experimental measurement data with reduced oversampling. The real part of the image (shown as an isosurface) corresponds to the reconstructed Bragg electron density, while the complex part of the image (gradient map projected onto the isosurface) corresponds to the reconstructed displacement field projection. In particular, FIG. 6(C) illustrates the t=66 min reconstructions for ½ of the required oversampling for w=0 and w=0.01, and the true solution, which is reconstructed using the complete data set.

FIG. 8(A) illustrates normalized modulus error evolution for the eight reconstructed time states for noise free sufficiently oversampled data. In particular, FIG. 8(A) illustrates normalized modulus error as a function of iteration number for w=0.

FIG. 8(B) illustrates normalized modulus error evolution for the eight reconstructed time states for noise free sufficiently oversampled data. In particular, FIG. 8(B) illustrates normalized modulus error as a function of iteration number for w=0:5.

FIG. 9(A) illustrates cross sections of reconstructions from real data showing the amplitude and phase for two time states with ½ the required oversampling for t=12 minutes. The images shown are cross sections of the states shown as isosurfaces in FIG. 6. Shown are w=0 and w=0.01. The true solution, reconstructed with the full data set, is also shown.

FIG. 9(B) illustrates cross sections of reconstructions from real data showing the amplitude and phase for two time states with ½ the required oversampling for t=42 minutes. The images shown are cross sections of the states shown as isosurfaces in FIG. 6. Shown are w=0 and w=0.01. The true solution, reconstructed with the full data set, is also shown.

FIG. 10(A) shows results for a time sequence consisting of t=0; 18; 34, 50; 66; and 76 minutes.

FIG. 10(B) shows results for a time sequence consisting of t=0; 34; 66; and 76 minutes.

FIG. 10(C) shows results for a time sequence consisting of t=0; 34; and 76 minutes.

FIG. 11(A) shows results for a time sequence consisting of t=0, 6, 10, 14, 18, 22, 26, 30, 34, and 38 minutes.

FIG. 11(B) shows results for a time sequence consisting of t=0, 2, 4, 6, 8, 10, 12, 14, 16, and 18 minutes.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Referring, in general, to the figures, a method for phase retrieval for sparse measurement sampling during dynamic processes is provided. As used herein, "dynamic processes" refers to a process in which the structure or position of an object to be imaged changes with time. For most physical processes, structural evolution is a continuous process that introduces structural redundancy when measured as a time series. The method described in the embodiments of the present application exploit this redundancy to allow for reduced oversampling (i.e., less than the conventionally required factor of 2), thereby improving the measurement rate. This method (hereinafter referred to as "chrono CDI") improves the temporal resolution of BCDI by reducing the oversampling requirement along one dimension ($q_z$) at a given time step without significantly compromising image fidelity. As used herein, image fidelity means that the reconstructed image is still interpretable. One method of quantitatively determining whether image fidelity is maintained is to sum the errors (i.e., the difference between the real and reconstructed image) on a pixel by pixel basis between the real image (i.e., an image based on a data set sampled at the Nyquist frequency) and the reconstructed image, and determine whether the sum exceeds a predetermined level of acceptable error. This can be done in real or reciprocal space. In one example, the predetermined level of acceptable error is less than or equal to 10% per pixel.

Figure 12:
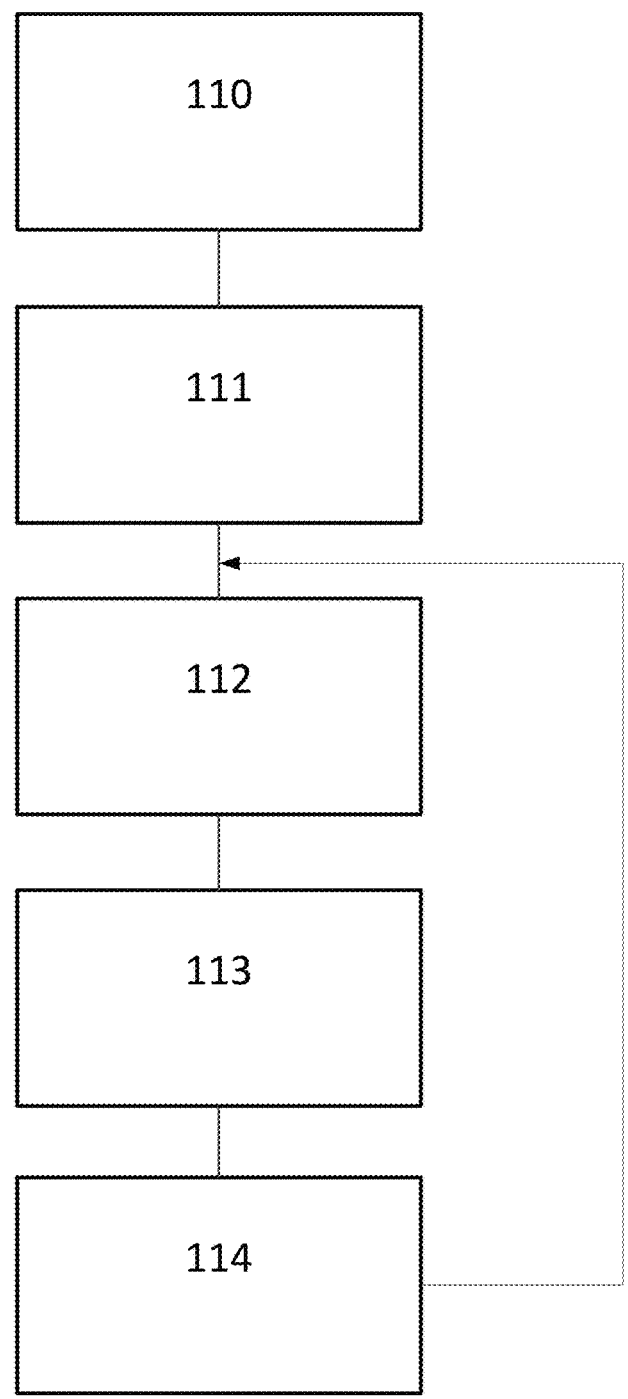
FIG. 12 is a flowchart illustrating the steps of a chrono CDI algorithm (method for phase retrieval) for sparse measurement sampling during dynamic processes.

In one embodiment (see FIG. 12), according to a process 100, a 3D data set $D_t$ is acquired for a single time state $\rho_t$. In Step 110, a coherent beam illuminates an object to be imaged. In Step 111, the beam scattered by the object produces a first diffraction pattern $DP_1$ that is measured by an area detector. In Step 112, the object is rotated around a tilt axis. In Step 113, the coherent beam illuminates the object (at a different position than Step 110 due to the rotation of the object). In Step 114, a second diffraction pattern $DP_2$ is measured by the area detector. Steps 112-114 are repeated for a predetermined number of times such that a sequence of 2D diffraction patterns are measured at different sample orientations. In other words, The sequence of 2D diffraction patterns (i.e., the 2D data collected from Steps 110, 111 and all repetitions of Step 112-114) are stacked to form a 3D data set $D_t$ measured at a single time state $\rho_t$. In others, the 3D data set $D_t$ includes each of the diffraction patterns $DP_1, DP_2, DP_3 \ldots DP_n$ collected at each position of the object during the time state $\rho_t$. The time between the acquisition of each diffraction pattern $DP_1, DP_2, DP_3 \ldots DP_n$ is equal to the time it takes to reposition the object (Step 112), re-illuminate the object with the coherent beam (Step 113), and measure the resulting diffraction pattern (Step 114).

In the chrono CDI method, the process 100 is repeated a predetermined number of times in order to obtain a 3D data set for each of a plurality of time states $\rho_1, \rho_2, \rho_3, \ldots \rho_n$. The number of time states required depends on the dynamics of the process. Typically, the process needs to be one order of magnitude slower than the time it takes to obtain a single 3D data set (i.e., one order of magnitude slower than $\rho_t$). To explain, a 3D data set $D_{t1}$ is obtained for a first time state $\rho_t$, no measurements are acquired for an interval of time $T_{rest}$, a 3D data set $D_{t2}$ is obtained for a second time state $\rho_2$, no measurements are acquired for the interval of time $T_{rest}$, and the process is repeated until a 3D data $D_{tn}$ is obtained for a time state $\rho_n$. The interval of time $T_{rest}$ between each time state is selected based on how rapidly the structure of the object is changing in the dynamic process. In particular, the faster the structure of the object is changing, the smaller the time $T_{rest}$. The slower the structure of the object is changing, the larger the time $T_{rest}$.

In one example, the 2D diffraction patterns that comprise the 3D data set $D_t$ are collected continuously with the time between acquiring different measurements in the 3D data set being about 10-20 seconds. The time it takes to acquire the entire 3D data (i.e., the duration of a single time state $\rho_t$) may be, for example, 6 minutes. The time $T_{rest}$ between each time state $\rho_t$ may be, for example, the time it takes to reposition the object to the position in which the object was provided when the first diffraction pattern $DP_1$ was measured in the first time state $\rho_1$ (e.g., 15-30 seconds) or longer.

After a 3D data set $D_t$ is acquired for each time state $\rho_t$, the data is processed by a computer programmed to reconstruct a 3D image of the object that shows the structure of the object at any given time state $\rho_t$.

In one example, Steps 110-114 are steps performed in BCDI. FIG. 1(A) shows a schematic of a Bragg rocking curve. In Step 110, a coherent x-ray beam $k_i$ illuminates an object to be imaged (e.g., a nanocrystal) and in Step 111, the beam scattered by the object produces a first diffraction pattern (e.g., in an area detector plane 1) that is measured by an area detector. Creating the rocking curve entails rotating the sample with respect to the incident x-ray beam $k_i$, illuminating the object with the coherent x-ray beam $k_i$, and measuring a subsequent diffraction pattern (e.g., in an area detector plane 2) using the area detector (Steps 112-114). The sample rotation, labeled schematically by $\theta_{start}$ and $\theta_{end}$, displaces the scattering vector $q=k_f-k_i$ from the reciprocal-space lattice point $G_{hkl}$, the Bragg reflection condition for the HKL lattice planes, so that the 3D intensity distribution can be appropriately sampled and the structure of the nanocrystal can be reconstructed. The series of 2D measurements from each of the area detector planes 1-7 are stacked to form a 3D data set $D_t$, where t represents a time index in a series of sequential rocking-curve measurements. As discussed above, the 3D data set $D_t$ includes each of the diffraction patterns $DP_1, DP_2, DP_3 \ldots DP_n$ collected at each position of the object (i.e., each of the area detector planes 1-7) during a single time state $\rho_t$. In the chrono CDI method of the present application, the number of diffraction patterns $DP_1, D_2, DP_3, \ldots DP_n$ that comprise the 3D data set $D_t$ for each time state $\rho_t$ can be reduced while still maintaining the fidelity of the reconstructed 3D image of the object.

Conventional phase retrieval algorithms require an oversampling of at least two of the diffraction patterns in all three dimensions. In addition, the nanocrystal must be approximately static over the measurement time (i.e., time state) $\rho_t$ while $D_t$ is collected, which limits the dynamic time scale that can be observed. Each time state $\rho_t$ is considered independently. Due to these requirements all 2D measurements (i.e., in area detector planes 1-7 in FIG. 1(A)) must be taken. Reduction in the number of measurements (i.e., omission of the data from any one of the detector planes 1-7) would result in a blurry image. As discussed above, for conventional phase retrieval algorithms, the pattern must be sampled at twice the Nyquist frequency to satisfy the oversampling requirements. For example, for 100-500 nm nanocrystals, approximately 60-80 measurements (slices) are required.

In contrast, in chrono CDI, to improve the time resolution, only some 2D measurements (for example, every other diffraction pattern $DP_1, DP_2, DP_3 \ldots DP_n$ as indicated by the asterisks in FIG. 1(A)) could be taken. The number of measurements (i.e., diffraction patterns) measured per each time state $\rho_t$ in chrono CDI is less than a number of measurements (i.e., diffraction patterns) measured in conventional phase retrieval algorithms without comprising the fidelity of the reconstructed 3D image. The reduction in the number of measurements required in chrono CDI is possible because information from each time state $\rho_1, \rho_2, \rho_3, \ldots \rho_n$ is used in the reconstruction of a 3D image for any given time state $\rho_t$. In other words, in chrono CDI, the reconstruction of the 3D image is dependent on the diffraction patterns obtained in every time state $\rho_t$, unlike the conventional phase retrieval algorithms which consider each time state $\rho_t$ independently. In other words, in chrono CDI, the number of measurements taken while still maintaining image fidelity can be reduced to a number below the oversampling requirement (i.e., a number less than the Nyquist frequency). The faster the dynamic process, the fewer number of measurements can be eliminated, and the slower the dynamic process, the greater number of measurements can be eliminated. This is due to the nearest neighbor correlation (described below).

To illustrate an example of structure of the object changing in the dynamic process, FIG. 1(B) shows a reconstructed image from data acquired at three selected time states during which a single crystal palladium (Pd) nanocube (85 nm side length) is exposed to hydrogen gas. Palladium nanocubes were synthesized by using a wet chemistry method and then spin casted onto a silicon substrate for the measurement. The average nanocube side length is 85 nm. A double crystal monochromator was used to select x-rays with a photon energy of 8.919 keV with 1 eV bandwidth and longitudinal coherence length of 0.7 μm. A set of Kirkpatrick Baez mirrors was used to focus the beam to approximately 1.5×1.5 μm². The silicon substrate was placed into a gas flow cell. The detector was set to a (111) Pd Bragg peak angle and the sample was scanned in the x-ray beam until a (111) Pd diffraction peak illuminated the detector. The particles are randomly oriented and therefore typically at most one diffraction pattern illuminates the area detector.

The rocking curve around the (111) Bragg reflection was collected by recording 2D coherent diffraction patterns with an x-ray sensitive area detector (Medipix 3, 55 μm pixel size) placed at 0.26 m away from the sample around an angle of 2Θ=36 deg. An angular range of (ΔΘ=±0:15 deg) was sampled at 51 equally spaced intervals. The total time for each 3D measurement was approximately 2 minutes. Two to three full 3D datasets were taken for each palladium nanocrystal in a helium environment. The 3.6% mole fraction $H_2$ gas in He was then flowed to increase the partial pressure of $H_2$ above zero. A Mylar window on the gas flow cell allows for a pressure slightly greater than atmospheric pressure. The pressure was left constant while 3D datasets were continuously collected at approximately 2-minute intervals.

The absolute value of the image corresponds to the Bragg-diffracting electron density, while the phase φ of the image is proportional to a component of the vector displacement field u via φ=u·Q. In this case, the Pd (111) Bragg peak was measured and φ~$u_{111}$. In the Pd nanocube, hydrogen intercalation initially causes displacement field changes (t=42 min) before morphological changes occur (t=76 min) due to the hydriding phase transformation. The time evolution of the nanocube structure shown in FIG. 1(B) was determined from BCDI experiments performed with an oversampling of 3 in $q_z$ at Sector 34-ID-C of the Advanced Photon Source at Argonne National Laboratory. Each complete measurement took approximately 2 minutes.

After the data is acquired, the data is processed to reconstruct a 3D image. In order to recover the phase information, Fourier-based iterative phase retrieval algorithms are utilized. In conventional phase retrieval algorithms, the disagreement or error between measurement and image Fourier transform is minimized. In particular, the function minimized by the error reduction phase retrieval algorithms is the modulus error $\varepsilon_M^2$, which measures the agreement between the reconstruction's Fourier moduli and the measured moduli, $$\varepsilon_M^2(\rho, D) = \sum_q \left| |\tilde{\rho}| - \sqrt{D} \right|^2, \quad |$$

where ρ is the 3D reconstructed object (in real space), D is the 3D far-field intensity measurement, q is the reciprocal-space coordinate, $\tilde{\rho} = \mathcal{F}[\rho]$, and $\mathcal{F}$ is the Fourier transform. Different choices of the function to be minimized lead to different phase retrieval algorithms. Conventional phase retrieval algorithms utilize data from a single time state (i.e., data collected in the measurement time $\rho_t$).

As discussed above, in the chrono CDI method of the present application, a plurality of 3D data sets $D_t$ are acquired, one for each of a plurality of time states $\rho_t$. The entire measurement time series (every data set $D_t$ from every time state $\rho_t$), which is typically a continuous physical process, is incorporated into a chrono CDI phase retrieval algorithm that allows the oversampling requirement at each time step to be reduced. The chrono CDI algorithm includes a miscorrelation term that depends on reconstructions at other time states, described according to Equation 1 below:

$$\sum_t \left[ \varepsilon_M^2(\rho_t, D_t) + \sum_{t' \neq t} w(t, t') \mu(\rho_t, \rho_{t'}) \right]. \quad (1)$$

In this expression, t indexes the time states, w(t, t') is the weight, t≠t', and μ(ρt, ρt') is the miscorrelation term. In Equation 1, the first term in the bracket measures the agreement between the measured data and the reconstructed image The second term in the bracket describes how similar the time states are to one another. The second term in the bracket represents the correlation between the time states. The nearest-neighbor correlations in time, is considered to be a scalar weight parameter w≥0, and a functional form for the miscorrelation of $$\mu(\rho_t, \rho_{t'}) = \sum_r |\rho_t - \rho_{t-1}|^2 + \sum_r |\rho_t - \rho_{t+1}|^2.$$

The tth term of Equation 1 then becomes:

$$\varepsilon_M^2(\rho_t, D_t) + w \left( \sum_r |\rho_t - \rho_{t-1}|^2 + \sum_r |\rho_t - \rho_{t+1}|^2 \right). \quad (2)$$

Although other forms are possible, this form has the advantage of being computationally inexpensive. The iterative algorithm is derived by minimizing Equation 2 summed over t.

An example of the algorithm for both the error reduction like and hybrid input output like update steps can be seen in the Matlab pseudocode below:

if ERflag=1
% error reduction step
rho(:,:,:,qq)=(1/(1+2*weights))*support(:,:,:,qq).*(Pmrho(:,:,:,qq)+ . . .
(weights)*(rho(:,:,:,qq+1)+rho(:,:,:,qq−1)));
else
% HIO:
cterm=2*rho(:,:,:,qq)−rho(:,:,:,qq+1)−rho(:,:,:,qq−1);
sc=1−support(:,:,:,qq);
rho(:,:,:,qq)=support(:,:,:,qq).*Pmrho(:,:,:,qq)+ . . .
sc*(rho(:,:,:,qq)−beta*Pmrho(:,:,:,qq))− . . .
weights*support(:,:,:,qq).*cterm;
end where qq indexes the time variable, rho is the current best guess for the reconstruction, support is the current support used, Pmrho(:,:,:,qq)=(ifftn(fftshift(Psi mod(:,:,:,qq)))), with Psi mod(:,:;:,qq)=data(:,:,:,qq).*exp(li*angle(Psi2(:,:,:,qq))); and Psi2(:,:,:,qq)=fftshift(fftn((rho(:,:,:,qq))));

To evaluation the performance of the chrono CDI algorithm, iterative phase retrieval was carried out on noise-free, simulated data, as well as on measured experimental data with different amounts of oversampling.

Simulated Data With Required Oversampling

Figure 2:
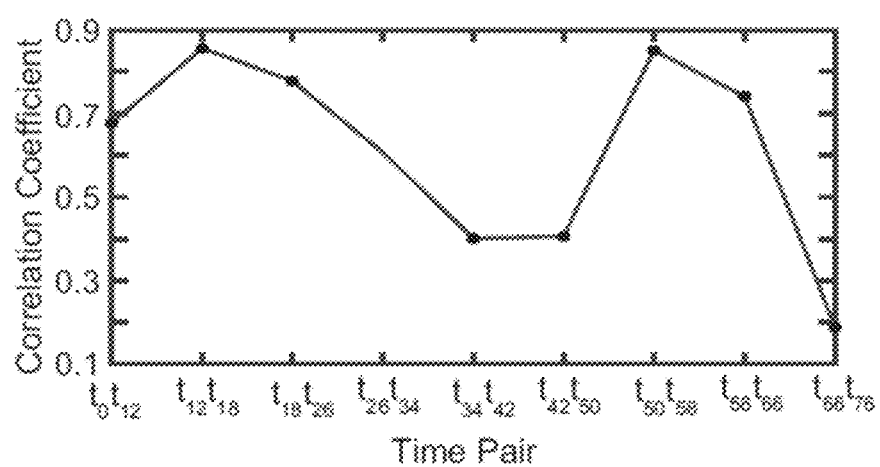
FIG. 2 illustrates a nearest-neighbor correlation coefficient of $u_{111}(r)$ for all pairs in the chosen time sequence. The average nearest-neighbor correlation coefficient is 61%.

In this case, the simulated data $D_t^{sim}$ are generated by 3D Fourier transforms of each complex valued Pd nanocube reconstruction in the time series after zero padding to meet the oversampling (OS) requirements of phase retrieval. As discussed above, as used in this application, an oversampling of 2 is used as the required oversampling. In practice, this means the cube size was half of the array size in all three dimensions. The time sequence (i.e., different time states) considered consists of t=0, 12, 18, 26, 34, 42, 50, 58, 66, and 76 minutes. This time sequence is approximately equally spaced and, as shown in FIG. 2, has varying amounts of nearest-neighbor correlation, with an average nearest-neighbor correlation coefficient of 61%. The correlation coefficient c(t,t')∈[−1, 1] is defined between two 3D displacement fields at time states t and t' by $$\frac{\sum_r [u_{111}(r, t) - \bar{u}_{111}(r, t)][u_{111}(r, t') - \bar{u}_{111}(r, t')]}{\sqrt{\sum_r [u_{111}(r, t) - \bar{u}_{111}(r, t)]^2} \sqrt{\sum_r [u_{111}(r, t') - \bar{u}_{111}(r, t')]^2}},$$

where $u_{111}$ is the displacement field projection and $\bar{u}_{111}$ is the average displacement field over the particle.

FIG. 3(A) shows the correlation coefficient matrix for the chosen time sequence. FIG. 2 is a plot of the superdiagonal matrix values. The chosen time sequence is a good balance between having a smooth evolution between nearest neighbors and having a large change over the whole time sequence (both the displacement and the amplitude change significantly). The first numerical test of chrono CDT reconstructs the sequence $\rho_t$ from the sequence of $D_t^{sim}$ with the required oversampling.

The algorithm uses random initial starts and alternates between the error reduction (ER) and the hybrid input-output (HIO) algorithms using a feedback parameter of β=0.7; the support is fixed to the size of the object and is not evolved during the iterative process. At iteration numbers N=100n, for n=1, 2, . . . , 18, the algorithm tests whether all reconstructions are correctly oriented with respect to the known initial (t=0 min) and final (t=76 min) states by testing whether they are conjugated and reflected ("twin") solutions. In order to have a known initial state and final state, the initial and final states are measured with the traditional number of measurements that satisfy the oversampling requirements (i.e., at the Nyquist frequency). Although reconstructing the "twin" image does not affect $\varepsilon_M^2$, it will negatively impact μ, resulting in an artificially high total objective. One constraint used is that the $\rho_t$ of the initial and final states are known in real and diffraction space. This constraint can be achieved by measuring diffraction data sets at the required oversampling before the experimental dynamics start and after no significant changes are seen in the diffraction data.

FIG. 3(B) shows the errors $\varepsilon_M^2(\rho_t, D_t^{sim})$ and μ(ρt, ρt'), averaged over all reconstructed time states and over ten random starts, as a function of the scalar weight w. Both errors are normalized by the total intensity in the image. FIGS. 8(A) and 8(B) show the modulus error $\varepsilon_M^2$ as a function of iteration number for two scalar weight values for eight reconstructed time states for noise free sufficiently oversampled date. In particular, FIG. 8(A) illustrates the normalized modulus error as a function of iteration number for w=0, while FIG. 8(B) illustrates the normalized modulus error as a function of iteration number for w=0.5. The initial and final states (t=0 and t=76 min, respectively) are known in real space. When w=0, the modulus error is the lowest, and the miscorrelation term is the largest. These results are expected because the data are noise free and oversampled at the required oversampling such that a unique solution is fully determined for each $D_t^{sim}$. The weight w=0 corresponds to the case when no correlations are taken into account. As w increases, $\mu(\rho_t, \rho_t')$ decreases, and $\varepsilon_M^2$ increases for the solution set $\{\rho_t\}$ because their relative contributions to the total objective change. With data sampled at the required oversampling, including information from neighboring time steps in a time series will not improve each individual reconstruction because the complete 3D structural description of the sample at each time is uniquely encoded in the 3D coherent intensity pattern.

Simulated Data With Reduced Oversampling

Next, the inventors explored how the additional redundancy from the time series can compensate for reduced oversampling during the rocking curve (e.g., oversampling at less than a factor of 2) at a given time step by reconstructing the time series $D_t^{sim}$ t discussed previously, but with different degrees of reduced sampling in $q_z$. To start, every third 2D diffraction measurement of the original 84 2D diffraction measurements was selected to form $D_t^{sim}$ for all times except the initial and final time. This leads to data that have ⅓ of the required oversampling. If such a time series were measured experimentally, the measurement time would be reduced by a factor of 3. In assessing algorithm performance, the modulus error was calculated by comparing the far-field exit wave of the reconstructions with the data sampled at the required oversampling. As before, the initial and final states are known, the support is known, and alternating ER/HIO is used as described previously.

Figure 4A:
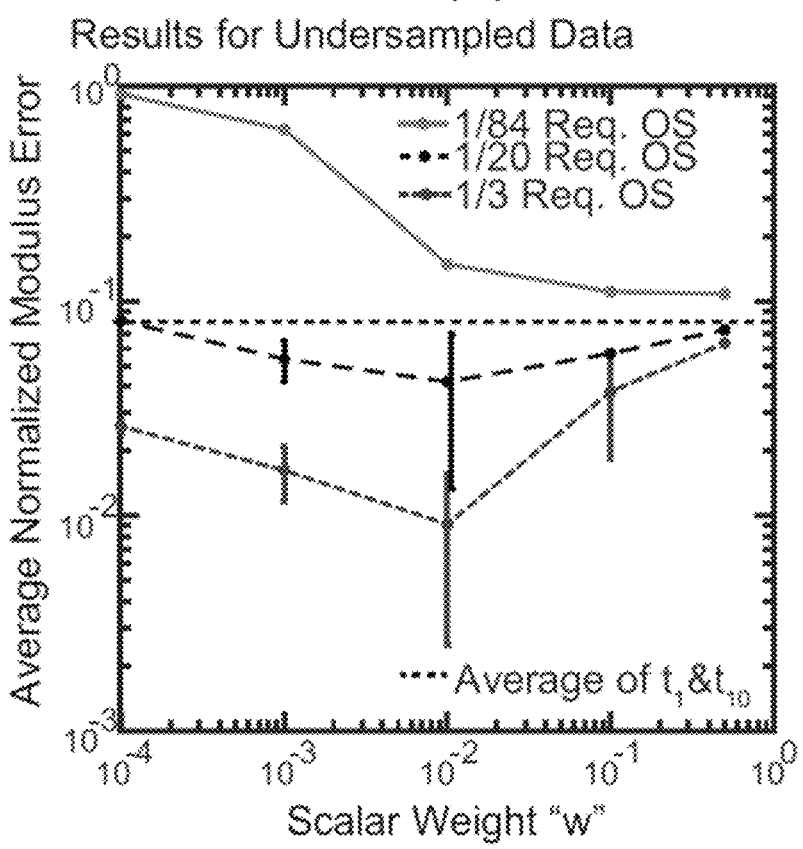
FIG. 4(A) illustrates the results for reduced oversampling. In particular.

FIG. 4(A) shows the average (over all time states and random starts) modulus error as a function of the scalar weight w for varying amounts of oversampling. The average normalized modulus error does not change from w=0 to w=10$^{-4}$. Unlike the results using the required oversampling (see FIG. 3(B)) where the lowest modulus error occurs for w=0 (no time correlation), in the cases where $q_z$ has been sampled at ⅓ (bottom line of FIG. 4(A)) and 1/20 (middle line of FIG. 4(A)) of the required oversampling, a minimum in the modulus error is observed at a value of w=0.01. This modulus error is computed with respect to the data sets that are sampled at the required oversampling, and thus the reconstructions at these minima are the "best" solutions. When only 1/84 (top line of FIG. 4(A)) of the required oversampling is used (i.e., a single slice from the rocking curve), the modulus error decreases with increasing w and approaches a constant value, which is near the normalized average modulus error when all the reconstructed time states are set to the average of the initial and final state (black dashed horizontal line). In this case, simply using an average of the initial and final states outperforms the reconstruction algorithm, indicating that there are insufficient reciprocal space constraints and that the oversampling in $q_z$ is too low.

On average, w=0.01 improves the reconstructed time sequence relative to w=0, which takes no time correlation into account, for up to 1/20 of the required oversampling. However, it is not clear from the plot of the average whether all time states are being improved equally. FIG. 4(B) shows the normalized modulus error at each time state for w=0, 0.01, and 0.5 at ⅓ of the required oversampling for a particular random start. The states nearest to the known states (t=0 and t=76 min) have lower modulus errors, as expected. By comparing w=0 with w=0.01, we see that the improvement occurs in all the intermediate states except the state at t=66 min, which remains essentially unchanged. These results demonstrate that the algorithm improves all reconstructions, even those least correlated with their neighbors (see FIG. 2 for a plot of the nearest-neighbor correlation). The benefits of chrono CDI are clear when the required oversampling is reduced by up to a factor of approximately 1/20. In these cases, enforcing a degree of nearest-time-step, real-space correlation provides an additional constraint that improves the reconstruction at all intermediate times relative to what can be achieved using conventional phase retrieval. Finally, all of the reconstructions on simulated data were rerun with an unknown support that was updated via the "shrink-wrap" algorithm to make a better comparison with the experimental data. The conclusions discussed previously remain valid.

Experimental Date

Figure 5:
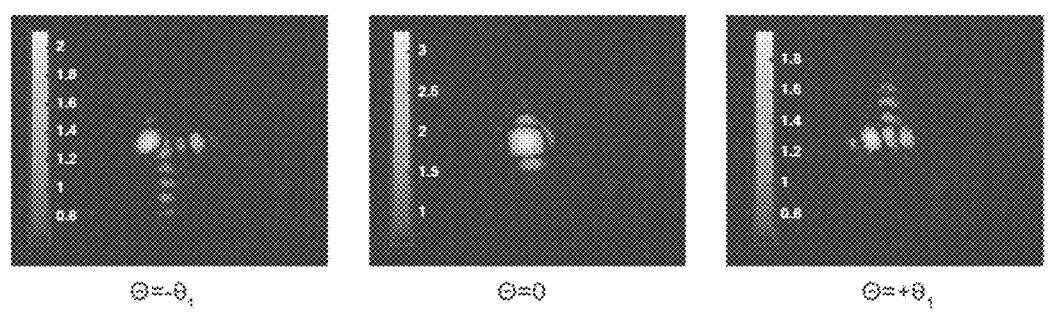
FIG. 5 illustrates three cross sections of the real data from t=12 min used to test the chrono CDI algorithm. The scale is the $\log_{10}$ of the number of photons. The data is oversampled by a factor of 3 in $q_z$ and has both noise and a finite scattering extent. These measured data sets, after background subtraction (1-2 photons) and the removal of a number of 2D slices, are used to test the chrono CDI algorithm.

Next, chrono CDI was demonstrated on experimental rocking curve data. To simulate varying degrees of reduced oversampling, a subset of the original 2D measurements was selected from the experimental data sets. FIG. 5 shows example 2D experimental diffraction measurements from the Pd (111) Bragg rocking curve. An oversampling of approximately 3 in qz was used during the original measurement. The reconstruction algorithm is the same as described previously, except that the support is not known a priori. Instead, an initial box half the array size in each dimension is used, and the support is updated with the shrink-wrap algorithm using a Gaussian function with a threshold of 0.01 and standard deviation of 1.

FIGS. 6(A) and 6(B) show chrono CDI reconstructions for two representative time states of experimental diffraction data from Pd nanocubes undergoing structural transformations when exposed to hydrogen gas. As before, different amounts of oversampling were investigated. The isosurfaces shown correspond to the reconstructed Bragg electron density, while the color map corresponds to the image phase φ, which is proportional to the u111 displacement field. FIG. 6(A) shows reconstructions when ½ of the required oversampling in $q_z$ is used. Every third slice of the original data (oversampled at a factor of 3 in $q_z$) was used to generate data. This corresponds to an oversampling of 1, which is ½ the required oversampling of 2. The reconstruction for w=0.01 is much improved compared with w=0 and is similar in morphology and lattice displacement to the true solution. The true solution is reconstructed using the complete data set. FIG. 6(B) shows that the same conclusion holds for t=42 min. FIG. 9 illustrates central cross sections that show the amplitude and phase distributions inside the crystal. The average normalized modulus error of the time sequence is improved from 0.2 to 0.1 by including nearest-neighbor information (via w=0.01). Although the reconstructions do not match exactly, the results convey the same overall physical changes in the crystal.

Figure 7:
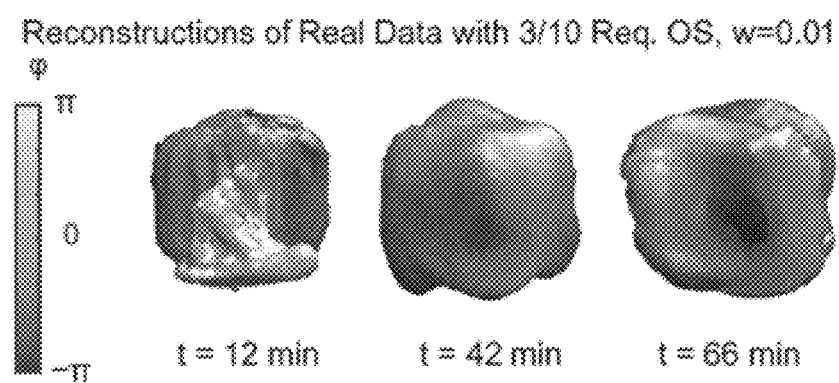
FIG. 7 illustrates reconstructions of real measurement data with 3/10 of the required oversampling and w=0.01. The real part of the image (shown as an isosurface) corresponds to the reconstructed Bragg electron density, while the complex part of the image, φ, is proportional to the displacement field projection. Three states from the reconstructed time sequence are shown.

FIG. 7 shows that when 3/10 of the required oversampling is used (corresponding to every fifth slice of the original data), major differences in both the reconstructed Bragg electron density and displacement fields arise as compared with the full-rocking-curve reconstructions. There are also disagreements in the reconstructed phases (proportional to the displacements). Thus, the chrono CDI applied to this particular set of measurement data for the chosen time sequence could have decreased the measurement time by a factor of 2 without losing the essential physics of the transforming crystal. For simulated data it could have reduced the time by up to a factor of 20. The discrepancy is due to the finite scattering extent in reciprocal space of the real data in addition to noise.

The success of the algorithm is directly tied to how correlated the intermediate time states are among themselves and to the initial and final states. This correlation can be tuned by changing the time scale of the dynamics in the experiment or by taking finer time steps. More correlated time sequences will lead to larger optimal w values and to better improvement in temporal resolution, while less correlated time series will lead to smaller optimal w values and to less improvement in temporal resolution.

Figure 10A:
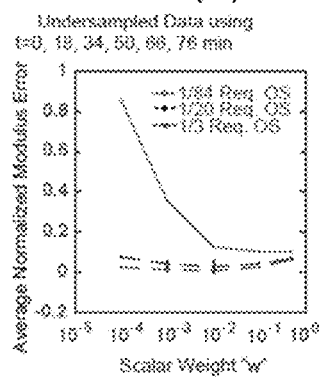
FIG. 10(A) illustrates the average (over all time states and random starts) normalized modulus error as a function of the scalar weight w for ⅓, 1/20, and 1/84 of the required oversampling. The modulus error reported here is computed with respect to the data with the required oversampling. Error bars represent the standard deviation of the different average (over all time states) values obtained from 10 different random starts. In particular.
Figure 10B:
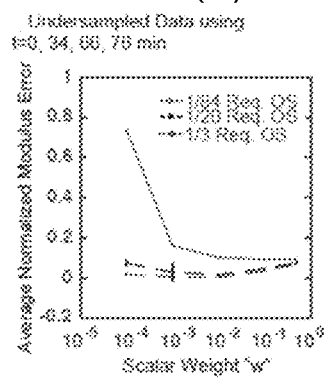
FIG. 10(B) illustrates the average (over all time states and random starts) normalized modulus error as a function of the scalar weight w for ⅓, 1/20, and 1/84 of the required oversampling. The modulus error reported here is computed with respect to the data with the required oversampling. Error bars represent the standard deviation of the different average (over all time states) values obtained from 10 different random starts. In particular.
Figure 10C:
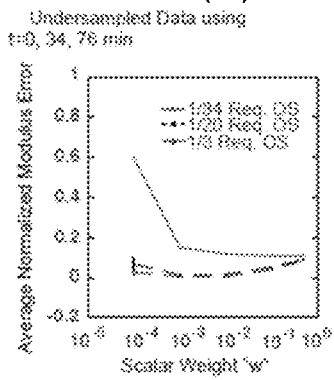
FIG. 10(C) illustrates the average (over all time states and random starts) normalized modulus error as a function of the scalar weight w for ⅓, 1/20, and 1/84 of the required oversampling. The modulus error reported here is computed with respect to the data with the required oversampling. Error bars represent the standard deviation of the different average (over all time states) values obtained from 10 different random starts. In particular.

Additional time sequences with different numbers of intermediate time are illustrated in FIGS. 10(A)-10(C). In particular, FIGS. 10(A)-10(C) illustrate the average (over all time states and random starts) normalized modulus error as a function of the scalar weight w for ⅓, 1/20, and 1/84 of the required oversampling. w=0 (not shown) produces the same average normalized modulus error values as $w=10^{-4}$. The modulus error reported here is computed with respect to the data with the required oversampling. Error bars represent the standard deviation of the different average (over all time states) values obtained from 10 different random starts. FIG. 10(A) shows results for a time sequence consisting of t=0, 18, 34, 50, 66, and 76 minutes. FIG. 10(B) show results for a time sequence consisting of t=0, 34, 66, and 76 minutes. FIG. 10(C) shows results for a time sequence consisting of t=0, 34, 76 minutes, FIGS. 10(A)-10(C) demonstrate that w=0.01 is fairly robust when less intermediate time states are used.

Figure 11A:
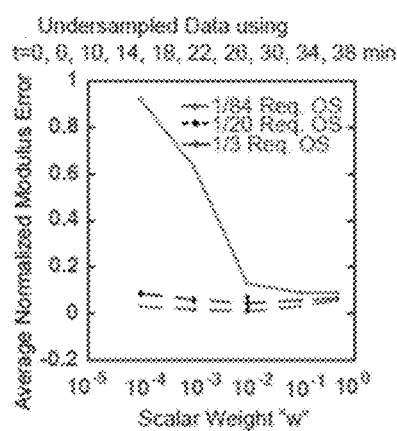
FIG. 11(A) illustrates the average (over all time states and random starts) normalized modulus error as a function of the scalar weight w for ⅓, 1/20, and 1/84 of the required oversampling. The modulus error reported here is computed with respect to the data with the required oversampling. Error bars represent the standard deviation of the different average (over all time states) values obtained from 10 different random starts. In particular.
Figure 11B:
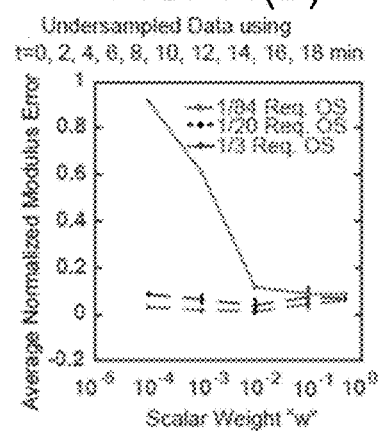
FIG. 11(B) illustrates the average (over all time states and random starts) normalized modulus error as a function of the scalar weight w for ⅓, 1/20, and 1/84 of the required oversampling. The modulus error reported here is computed with respect to the data with the required oversampling. Error bars represent the standard deviation of the different average (over all time states) values obtained from 10 different random starts. In particular.

FIGS. 11(A) and 11(B) illustrate the average (over all time states and random starts) normalized modulus error as a function of the scalar weight w for ⅓, 1/20, and 1/84 of the required oversampling. w=0 (not shown) produces the same average normalized modulus error values as $w=10^{-4}$. The modulus error reported here is computed with respect to the data with the required oversampling. Error bars represent the standard deviation of the different average (over all time states) values obtained from 10 different random starts. FIG. 11(A) shows results for a time sequence consisting of t=0, 6, 10, 14, 18, 22, 26, 30, 34, and 38 minutes. FIG. 11(B) shows results for a time sequence consisting of t=0, 2, 4, 6, 8, 10, 12, 14, 16, and 18 minutes. FIGS. 11(A) and 11(B) show that w=0.01 is fairly robust when different time sequences are used.

As discussed above, by incorporating the entire measurement time series, which is typically a continuous physical process, into phase retrieval allows the oversampling requirement at each time step to be reduced, leading to a subsequent improvement in the temporal resolution by a factor of 2-20 times. By incorporating the redundancy from the entire time series into each individual measurement, less time can be taken during each measurement and the time resolution is increased. The increased time resolution will allow imaging of faster dynamics and of radiation-dose-sensitive samples. Although use of the "chrono CDI" approach was discussed in conjunction with BCDI, the chrono CDI approach may find use in improving the time resolution in other imaging techniques.

As demonstrated above, the chrono CDI phase retrieval algorithm improves the time resolution of BCDI by a factor of 2 for experimental data and 20 for simulated data. The algorithm thereby enables BCDI investigations of faster processes and can be used to limit radiation dose. The time resolution improvements we demonstrate are achieved by reducing the number of 2D measurements made during a 3D Bragg rocking curve, leading to data sets with less than the required oversampling in qz at each intermediate time step. The rocking curves across the entire time series are reconstructed simultaneously, enforcing a degree of real-space correlation between solutions at neighboring time steps to account for the reduced oversampling of each individual measurement. In other embodiments, the algorithm and its variations may be useful for improving the time resolution of other imaging techniques, such as ptychography (ptychographic coherent imaging), tomography (e.g., CT scans), etc., where there is a continuous relationship in real space between nearest-neighbor time states.

The construction and arrangements of the method for phase retrieval, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, image processing and segmentation algorithms, etc. without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The chrono CDI algorithm/method described above may be executed by a computer programmed to perform the steps of the algorithm. Embodiments of the subject matter and the operations described in this specification can be implemented in digital electronic circuitry, or in computer software embodied on a tangible medium, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on one or more computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium may be tangible and non-transitory.

The operations described in this specification can be implemented as operations performed by a data processing apparatus or processing circuit on data stored on one or more computer-readable storage devices or received from other sources.

The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors or processing circuits executing one or more computer programs to perform actions by operating on input data and generating output. The processes and logic flows can also be performed by, and apparatus can also be implemented as, special purpose logic circuitry, e.g., an FPGA or an ASIC.

Processors or processing circuits suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display), OLED (organic light emitting diode), TFT (thin-film transistor), plasma, other flexible configuration, or any other monitor for displaying information to the user and a keyboard, a pointing device, e.g., a mouse trackball, etc., or a touch screen, touch pad, etc., by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

What is claimed:

1. A method for retrieving phase information in a coherent diffraction imaging process, the method comprising:
   acquiring a plurality of 3D data sets, each 3D data set corresponding to one of a plurality of time states, where each 3D data set is acquired using the following steps:
   illuminating an object to be imaged with a coherent beam, the object positioned in a first position;
   measuring a first 2D diffraction pattern using an area detector that detects a number of photons or electrons in a beam scattered by the object;
   rotating the object around a tilt axis thereof to a second position that is different from the first position;

re-illuminating the object with the coherent beam, the object positioned in the second position;

re-measuring a second 2D diffraction pattern using the area detector; and repeating the rotating, re-illuminating and re-measuring steps a predetermined number of times such that each 3D data set includes a predetermined number of diffraction patterns; and reconstructing a 3D image of the object at a given time state using information from the 3D data set from the given time state and all of the other time states, wherein the predetermined number of diffraction patterns in at least one 3D data set is less than a minimum number of 2D diffraction patterns required based on the Nyquist frequency; wherein the 3D image reconstructed based on the at least one 3D data set has image fidelity, where image fidelity is established when a sum of a difference between a real image and the 3D image reconstructed based on the at least one 3D data set on a pixel by pixel basis is less than or equal to a predetermined level of acceptable error.

2. The method according to claim 1, wherein the predetermined level of acceptable error is than or equal to 10% per pixel.

3. The method according to claim 1, wherein the predetermined number of diffraction patterns in at least one 3D data set is ⅓ of a minimum number of 2D diffraction patterns required based on the Nyquist frequency.

4. The method according to claim 1, wherein the plurality of 3D data sets include a 3D data set acquired at an initial time state, a 3D data set acquired at a final time state, and at least one 3D data set acquired at an intermediate time state between the initial time state and the final time state.

5. The method according to claim 4,
wherein the predetermined number of diffraction patterns in the initial time state is equal to a minimum number of 2D diffraction patterns required based on the Nyquist frequency,
wherein the predetermined number of diffraction patterns in the final time state is equal to the minimum number of 2D diffraction patterns required based on the Nyquist frequency, and
wherein the predetermined number of diffraction patterns in the intermediate time state is less than to the minimum number of 2D diffraction patterns required based on the Nyquist frequency.

6. The method according to claim 1, wherein the plurality of 3D data sets include a 3D data set acquired at an initial time state, a 3D data set acquired at a final time state, and a plurality of 3D data sets acquired at intermediate time states between the initial time state and the final time state.

7. The method according to claim 1, wherein the step of reconstructing the 3D image of the object is repeated for each of the plurality of time states to produce a series of 3D images that show a change in a structure of the object over time during a dynamic process.

8. The method according to claim 7, wherein structural changes that occur during the dynamic process occur at a rate that is one magnitude slower than a duration of each time state.

9. The method according to claim 1,
wherein the object is a nanocrystal having a size of 100-500 nm, and
wherein the step of reconstructing the 3D image of the nanocrystal is repeated for each of the plurality of time states to produce a series of 3D images that show a change in a structure of the nanocrystal over time.

10. The method according to claim 9, wherein the predetermined number of diffraction patterns in each of the 3D data sets is 60 to 80.

11. The method according to claim 1, wherein a duration of each time state is less than a duration of time needed to obtain a minimum number of 2D diffraction patterns required based on the Nyquist frequency.

* * * * *